United States Patent [19]
Herrmann et al.

[11] Patent Number: 6,025,343
[45] Date of Patent: Feb. 15, 2000

[54] LIPID ESTERS OF NUCLEOSIDE MONOPHOSPHATES AND THEIR USE AS IMMUNOSUPPRESSIVE DRUGS

[75] Inventors: Dieter Herrmann, Heidelberg; Hans-Georg Opitz, Weinheim; Harald Zilch, Mannheim; Alfred Mertens, Schriesheim, all of Germany

[73] Assignee: Roche Diagnostics GmbH, Mannheim, Germany

[21] Appl. No.: 08/753,633

[22] Filed: Nov. 27, 1996

Related U.S. Application Data

[63] Continuation-in-part of application No. PCT/EP95/01951, May 23, 1995.

[30] Foreign Application Priority Data

May 28, 1994 [DE] Germany ............................. 44 18 690

[51] Int. Cl.$^7$ .................................................. A01N 43/04
[52] U.S. Cl. .................. 514/46; 514/45; 514/47; 514/49; 514/50; 514/51; 514/885; 514/908; 536/26.7; 536/26.8
[58] Field of Search .................. 536/26.7, 26.8; 514/45, 46, 47, 49, 50, 51, 885, 908

[56] References Cited

U.S. PATENT DOCUMENTS 5,463,092 10/1995 Hostetler et al. ........................ 514/885
5,512,671 4/1996 Piantadosi et al. ..................... 536/26.8
5,563,257 10/1996 Zilch et al. ............................. 536/26.14

*Primary Examiner*—James O. Wilson
*Attorney, Agent, or Firm*—Nikaido Marmelstein Murray & Oram, LLP

[57] ABSTRACT

The present invention is directed to new nucleoside monophosphate derivatives of lipid ester residues of general formula (I)

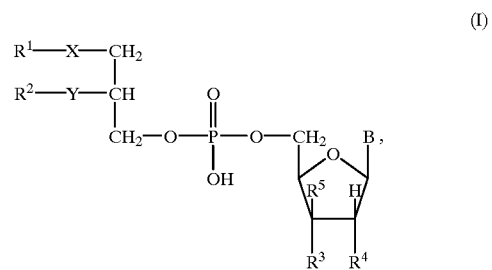

wherein $R^1$ represents an optionally substituted alkyl chain having 1–20 carbon atoms;

$R^2$ represents hydrogen, an optionally substituted alkyl chain having 1–20 carbon atoms;

$R^3$, $R^4$ and $R^5$ represent hydrogen, hydroxy, azido, amino, cyano, or halogen;

X represents a valence dash, oxygen, sulfur, a sulfinyl or sulfonyl group;

Y represents a valence dash, an oxygen or sulfur atom;

B represents a purine and/or pyrimidine base;

with the proviso that at least one of the residues $R^3$ or $R^5$ is hydrogen;

to their tautomers and their physiologically acceptable salts of inorganic and organic acids and/or bases, as well as to processes for their preparation, and to drugs containing said compounds.

25 Claims, 2 Drawing Sheets

Fig.2

LIPID ESTERS OF NUCLEOSIDE MONOPHOSPHATES AND THEIR USE AS IMMUNOSUPPRESSIVE DRUGS

CROSS REFERENCE TO RELATED APPLICATION

This application is a continuation-in-part of International Application PCT/EP95/01951, filed May 23, 1995, and designating the U.S.

The present invention is directed to new nucleoside monophosphate derivatives of lipid ester residues of general formula (I)

(I)

wherein
- $R^1$ may be a straight-chain or branched, saturated or unsaturated alkyl chain having 1–20 carbon atoms, optionally mono- or polysubstituted by halogen, $C_1$–$C_6$ alkoxy, $C_1$–$C_6$ alkylmercapto, $C_1$–$C_6$ alkoxycarbonyl, $C_1$–$C_6$ alkylsulfinyl, or $C_1$–$C_6$ alkylsulfonyl groups;
- $R^2$ may be hydrogen, a straight-chain or branched, saturated or unsaturated alkyl chain having 1–20 carbon atoms, optionally mono- or polysubstituted by halogen, $C_1$–$C_6$ alkoxy, $C_1$–$C_6$ alkylmercapto, $C_1$–$C_6$ alkoxycarbonyl, or $C_1$–$C_6$ alkylsulfonyl groups;
- $R^3$ represents hydrogen, hydroxy, azido, amino, cyano, or halogen;
- $R^4$ represents hydroxy, azido, amino, cyano, or halogen;
- $R^5$ represents hydrogen, hydroxy, azido, amino, cyano, or halogen;
- X represents a valence dash, oxygen, sulfur, a sulfinyl or sulfonyl group;
- Y is a valence dash, an oxygen or sulfur atom;
- B represents a purine and/or pyrimidine base of formula III(a–d)

(IIIa)

(IIIb)

(IIIc)

(IIId)

wherein
- $R^6$ may be hydrogen; an alkyl chain having 1–6 carbon atoms, which may be substituted by halogen; an alkenyl and/or alkinyl residue having 2–6 carbon atoms, optionally substituted by halogen; or halogen;
- $R^{6'}$ may be a hydrogen atom or a benzyl or phenylthio residue;
- $R^7$ may be hydrogen; an alkyl chain having 1–6 carbon atoms, which may be substituted by halogen; or halogen;
- $R^8$ may be hydrogen, an alkyl chain having 1–6 carbon atoms, halogen, or a hydroxy or an amino group;
- $R^9$ may be hydrogen, an amino group or a halogen atom; and
- $R^{10}$ may be hydrogen, halogen, mercapto, hydroxy, $C_1$–$C_6$ alkoxy, $C_1$–$C_6$ alkylmercapto, or an amino group which may be mono- or disubstituted by $C_1$–$C_6$ alkyl, $C_1$–$C_6$ alkoxy, hydroxy-$C_2$–$C_6$ alkyl, and/or $C_3$–$C_6$ cycloalkyl, aryl, hetaryl, aralkyl, or hetarylalkyl groups, optionally substituted at the aryl or hetaryl residue by one or more mercapto, hydroxy, $C_1$–$C_6$ alkoxy, or $C_1$–$C_6$ alkyl groups or halogen; or $C_2$–$C_6$ alkenyl optionally substituted by mono- or dialkyl or alkoxy groups;

with the proviso that at least one of the residues $R^3$ or $R^5$ is hydrogen;

to their tautomers and their physiologically acceptable salts of inorganic and organic acids and/or bases, as well as to processes for their preparation, and to drugs containing said compounds.

As these compounds of general formula I contain asymmetric carbon atoms, the invention is likewise directed to all the optically active forms and racemic mixtures of said compounds.

J. Biol. Chem. 265, 6112 (1990), and EP 0,350,287 describe preparation and use of liponucleotides as anti-viral drugs. Therein, however, only dimyristoylphosphatidyl and dipalmitoylphosphatidyl residues coupled to familiar nucleosides such as AZT (azidothymidine) and ddC (2',3'-dideoxycytidine) have been examined and synthesized, including their fatty acid ester structure.

J. Med. Chem. 33, 1380 (1990), describes nucleoside conjugates of thioether lipids with cytidine diphosphate, which have antitumor activity and might find use in oncology. Chem. Pharm. Bull. 36, 209 (1988), describes 5'-(3-sn-phosphatidyl)nucleosides having antileukemic activity, as well as their enzymatic synthesis from the corresponding nucleosides and phosphocholines in the presence of phospholipase D with transferase activity. Similarly, J. Med. Chem. 34, 1408 (1991), describes nucleoside conjugates having anti-HIV 1 activity, which are substituted by methoxy or ethoxy in sn-2 position of the lipid portion. The patent application WO 92/03462 describes thioether lipid conjugates having antiviral activity, particularly for treating HIV infections.

The compounds of the present invention have valuable pharmacological properties. In particular, they are suitable in therapy and prophylaxis of malignant tumors such as malignancies, neoplasms, carcinomas, sarcomas, or leukemias in tumor therapy. In addition, the compounds exhibit immunosuppressive activity and therefore, they may be employed in the therapy of organ-specific or generalized auto-immune diseases such as rheumatoid arthritis, systemic lupus erythematosus, chronic graft vs. host disease, multiple sclerosis, etc., or in preventing allogenic or semiallogenic graft rejection, e.g., kidneys, liver, lungs, heart, etc. Furthermore, the compounds have antiviral, anti-retroviral or anti-oncogenic activity and thus, are also suitable in prophylaxis and therapy of viral and oncogenic-induced/caused diseases (such as AIDS etc.). Compared to compounds hitherto employed in treatment of malign tumors, the compounds according to the invention have enhanced efficacy or lower toxicity and thus, have a wider therapeutic range. For this reason, they are advantageous in that the administration of drugs containing these compounds may be conducted continuously over a prolonged period of time, and withdrawal of the preparation or intermittent administration, which frequently has been routine with cytostatic agents hitherto employed in tumor therapy or, due to their undesirable side-effects, has been necessary, can be avoided.

The compounds according to the invention do not suffer from these drawbacks. Their action is immunosuppressive or antitumoral, without being unspecifically cytotoxic in pharmacologically relevant doses.

Similarly, the compounds of the present invention and their pharmaceutical formulations may be employed in combination with other drugs for the treatment and prophylaxis of the diseases mentioned above. Examples of these further drugs involve agents such as, e.g., mitosis inhibitors such as colchicine, mitopodozid, vinblastine, alkylating cytostatic agents such as cyclophosphamide, melphalan, myleran or cisplatin, antimetabolites such as folic acid antagonists (methotrexate) and antagonists of purine and pyrimidine bases (mercaptopurine, 5-fluorouridine, cytarabin), cytostatically active antibiotics such as anthracyclines (e.g., doxorubicin, daunorubicin), hormones such as fosfestrol, tamoxifen, other cytostatically/cytotoxically active chemotherapeutic agents and other immunosuppressive drugs (such as cyclosporines, FK 506, rapamycines, desoxyspergualin, etc.).

Above all, possible salts of the compounds of general formula I are the alkali, alkaline earth and ammonium salts of th phosphate group. Preferred as the alkali salts are lithium, sodium and potassium salt. Possible as the alkaline earth salts are magnesium and calcium, in particular. According to the invention, ammonium salts are understood to be those containing the ammonium ion which may be substituted up to four times by alkyl residues having 1–4 carbon atoms, and/or aralkyl residues, preferably benzyl residues. Here, the substituents may be the same or different.

The compounds of general formula I may contain basic groups, particularly amino groups, which may be converted to acid addition salts by suitable inorganic or organic acids. To this end, possible as the acids are, in particular: hydrochloric acid, hydrobromic acid, sulfuric acid, phosphoric acid, fumaric acid, succinic acid, tartaric acid, citric acid, lactic acid, maleic acid, or methanesulfonic acid.

In the general formula I, $R^1$ preferably represents a straight-chain $C_8$–$C_{15}$ alkyl group which may be further substituted by a $C_1$–$C_6$ alkoxy or a $C_1$–$C_6$ alkylmercapto group. More specifically, $R^1$ represents a nonyl, decyl, undecyl, dodecyl, tridecyl, or tetradecyl group. Preferably, methoxy, ethoxy, butoxy, and hexyloxy groups are possible as the $C_1$–$C_6$ alkoxy substituents of $R^1$. In case $R^1$ is substituted by a $C_1$–$C_6$ alkylmercapto residue, this is understood to be the methylmercapto, ethylmercapto, propylmercapto, butylmercapto, and hexylmercapto residue, in particular.

Preferably, $R^2$ represents a straight-chain $C_8$–$C_{15}$ alkyl group which may be further substituted by a $C_1$–$C_6$ alkoxy or a $C_1$–$C_6$ alkylmercapto group. More specifically, $R^2$ represents an octyl, nonyl, decyl, undecyl, dodecyl, tridecyl, or tetradecyl group. Preferably, methoxy, ethoxy, propoxy, butoxy, and hexyloxy groups are preferable as the $C_1$–$C_6$ alkoxy substituents of $R^2$. In case $R^2$ is substituted by a $C_1$–$C_6$ alkylmercapto residue, this is understood to be the methylmercaptot ethylmercapto, butylmercapto, and hexylmercapto residue, in particular.

Preferably, X is sulfur, sulfinyl or sulfonyl, and Y is oxygen.

Similarly, compounds are preferred, wherein X and Y represent a valence dash, $R^2$ is hydrogen, and $R^1$ represents a $C_1$–$C_{20}$ alkyl chain optionally substituted by $C_1$–$C_6$ alkoxy or $C_1$–$C_6$ alkylmercapto.

Preferably, $R^5$ represents hydrogen, azido, cyano or halogen, such as fluorine, chlorine or bromine.

Preferably, each $R^3$ and $R^4$ represent a hydroxy or a cyano or azido group, or a halogen atom, such as fluorine, chlorine, bromine or iodine, wherein the residues may be the same or different.

Particularly preferred are compounds, wherein $R^5$ represents a hydrogen atom and $R^3$ and $R^4$ are hydroxy, cyano, azido or fluorine.

In the bases of general formula (III) the residues $R^6$ and $R^7$ preferably represent a hydrogen atom, a methyl, trifluoromethyl, ethyl, propyl, or butyl residue, or a halogen atom, such as fluorine, chlorine, bromine or iodine, as well as an alkenyl and/or alkinyl group which may be substituted by halogen.

Particularly preferred for $R^6$ and $R^7$ is a hydrogen atom, the methyl, trifluoromethyl or ethyl residues, and a fluorine, chlorine or bromine atom, and/or the vinyl, propenyl, ethinyl or propinyl residues optionally substituted by halogen.

Preferably, the residue $R^8$ is a hydrogen atom, a methyl, ethyl, propyl, or butyl residue, an amino group or a halogen atom such as fluorine, chlorine bromine or iodine, preferably chlorine or bromine.

Preferably, $R^{10}$ represents a hydrogen, fluorine, chlorine or bromine atom, a $C_1$–$C_6$ alkoxy group, more specifically a methoxy, ethoxy, propoxy, butoxy, or hexyloxy group, a mercapto residue, a $C_1$–$C_6$ alkylmercapto group, more spe- cifically a methylmercapto, ethylmercapto, butylmercapto, or hexylmercapto group, or an amino group which may be mono- or disubstituted by a $C_1$–$C_6$ alkyl group, such as the methyl, ethyl, butyl or hexyl groups, by a hydroxy-$C_2$–$C_6$ alkyl group, such as the hydroxyethyl, hydroxypropyl, hydroxybutyl, or hydroxyhexyl groups, by a $C_3$–$C_6$ cycloalkyl residue, such as the cyclopropyl, cyclopentyl or cyclohexyl residues, by aryl, preferably phenyl, by an aralkyl residue, such as, in particular, benzyl optionally substituted by one or more hydroxy or methoxy groups, by $c_1$–$C_6$ alkyl groups, such as the methyl, ethyl, propyl, butyl, or hexyl groups, or by halogen atoms, such as fluorine, chlorine or bromine. Similarly, the amino group may be substituted by a hetarylalkyl or hetaryl residue such as, in particular, the thienyl, furyl or pyridyl residues, for example. Preferably, the hetaryl residue is understood to be the thienylmethyl, furylmethyl or pyridylmethyl residue.

Preferably, the following nucleosides are suitable as the coupling components to prepare the lipid-nucleotide conjugates of formula (I):

6-Mercaptopurine-9-β-D-ribofuranoside
5-Fluorouridine
Inosine
5-Methyluridine
2',3'-Didesoxy-2',3'-difluorothymidine
5-Chlorouridine
5-Trifluoromethyluridine
5-Ethinyluridine
5-Ethinylcytidine
5-Prop-1-enyluridine
5-Prop-2-enyluridine
Adenosine
Guanosine
2,6-Diaminopurine-9-β-D-ribafuranoside
2-Amino-6-mercaptopurine-9-β-D-ribofuranoside
2-Amino- 6-mercaptomethylpurine-9-β-D-ribofuranoside
2-Amino-6-chloropurine-9-β-D-ribofuranoside
2'-Desoxy-2'-aminoadenosine
2'-Desoxy-2'-azidoadenosine
2'-Desoxy-2'-azidocytidine
2'-Desoxy-5-fluorouridine
2-Chloroadenosine
2-Bromoadenosine
3'-Desoxy-3'-fluoroadenosine
6-Methylmercaptopurine-9-β-D-ribofuranoside
2-Fluoroadenosine
2-Fluoro-2'-desoxyadenosine

The compounds of general formula (I) may be prepared by

1. Reacting a Compound of General Formula V (V)

wherein $R^1$, $R^2$, X and Y have the meanings as indicated, with a compound of general formula VI (VI)

wherein $R^3$, $R^4$, $R^5$ and B have the above-mentioned meanings, or represent a hydroxy group protected by an oxygen protecting group familiar to the artisan, in the presence of an activating acid chloride, such as 2,4,6-triisopropylbenzenesulfonic acid chloride, and a tertiary nitrogen base, e.g., pyridine or lutidine, in an inert solvent, such as toluene, or immediately in anhydrous pyridine, and optionally, subsequent to hydrolysis, removing the oxygen protecting groups according to procedures conventional in nucleoside chemistry, or 2. Reacting a Compound of General Formula VII (VII)

wherein $R^1$, $R^2$, X and Y have the above-mentioned meanings, with a compound of general formula VI, wherein $R^3$, $R^4$, $R^5$ and B have the above-mentioned meanings, in the presence of phospholipase D from Streptomyces in an inert solvent such as chloroform, in the presence of a suitable buffer, and optionally, subsequent to reaction, removing the oxygen protecting groups according to procedures conventional in nucleoside chemistry.

The preparation of the compounds of general formula V and VII is performed in analogy to Lipids 22, 947 (1987), and J. Med. Chem. 34, 1377 (1991).

The preparation of the compounds of general formula VI is described, e.g., in EP-A-0,286,028 and WO 90/08147. Some of the included nucleosides are commercially available compounds.

Compounds similar to formula I are described in EP-A-0,350,287. Therein, the corresponding 1,2-diesters of glycerol are described.

The drugs containing compounds of formula I for the treatment of viral infections may be applied in liquid or solid forms on the intestinal or parenteral route. Here, the common application forms are possible, such as tablets, capsules, coated tablets, syrups, solutions, or suspensions. Preferably, water is used as the injection medium, containing additives such as stabilizers, solubilizers and buffers as are common with injection solutions. Such additives are, e.g., tartrate and citrate buffers, ethanol, complexing agents such as ethylenediaminetetraacetic acid and its non-toxic salts, high-molecular polymers such as liquid polyethylene oxide for viscosity control. Liquid vehicles for injection solutions need to be sterile and are filled in ampoules, preferably. Solid carriers are, for example, starch, lactose, mannitol, methylcellulose, talc, highly dispersed silicic acids, higher-molecular fatty acids such as stearic acid, gelatine, agar-agar, calcium phosphate, magnesium stearate, animal and plant fats, solid high-molecular polymers such as polyethylene glycol, etc. If desired, formulations suitable for oral application may include flavorings or sweeteners.

The dosage may depend on various factors such as mode of application, species, age, or individual condition. Conventionally, the compounds according to the invention are applied in amounts of 0.1–100 mg, preferably 0.2–80 mg per day and per kg of body weight. It is preferred to divide the daily dose into 2–5 applications, with tablets having an active ingredient content of 0.5–500 mg being administered with each application. Similarly, the tablets may have sustained release, reducing the number of applications to 1–3 per day. The active ingredient content of sustained-release tablets may be 2–1000 mg. The active ingredient may also be administered by continuous infusions, where amounts of 5–1000 mg per day are normally sufficient.

In addition to the compounds mentioned in the examples, the following compounds of formula I are possible in the meaning of the present invention:

1. (5-Chlorouridine)-5'-phosphoric acid (3-dodecylmercapto-2-decyloxy)propyl ester
2. (5-Trifluoromethyluridine)-5'-phosphoric acid (3-dodecylmercapto-2-decyloxy) propyl ester
3. (6-Mercaptopurine-9-β-D-ribofuranoside)-5'-phosphoric acid (3-dodecylmercapto-2-decyloxy)propyl ester
4. (5-Fluorouridine)-5'-phosphoric acid (3-dodecylmercapto-2-decyloxy)propyl ester
5. (5-Prop-1-enyluridine)-5'-phosphoric acid (3-dodecylmercapto-2-decyloxy) propyl ester
6. (5-Ethinylcytidine)-5'-phosphoric acid (3-dodecylmercapto-2-decyloxy)propyl ester
7. (2-Amino-6-mercaptopurine-9-β-D-ribofuranoside)-5'-phosphoric acid (3-dodecylmercapto-2-decyloxy)propyl ester
8. (2,6-Diaminopurine-9-β-D-ribofuranoside)-5'-phosphoric acid (3-dodecylmercapto-2-decyloxy)propyl ester
9. (5-Prop-2-enyluridine)-5'-phosphoric acid (3-dodecylmercapto-2-decyloxy)propyl ester
10. (5-Fluorouridine)-5'-phosphoric acid (3-dodecylsulfonyl-2-decyloxy)propyl ester
11. (5-Chlorouridine)-5'-phosphoric acid (3-dodecylsulfonyl-2-decyloxy)propyl ester
12. (6-Mercaptopurine-9-β-D-riboturanoside)-5'-phosphoric acid (3-dodecylsulfonyl-2-decyloxy)propyl ester
13. (5-Fluorouridine)-5'-phosphoric acid (3-dodecyloxy-2-decyloxy)propyl ester
14. (6-Mercaptopurine-9-β-D-ribofuranoside)-5'-phosphoric acid (3-dodecyloxy-2-decyloxy)propyl ester
15. (5-Fluorouridine)-5'-phosphoric acid (3-dodecylmercapto-2-decylmercapto)propyl ester
16. (5-Fluorouridine)-5'-phosphoric acid (3-undecylmercapto-2-undecyloxy)propyl ester
17. (5-Trifluoromethyluridine)-5'-phosphoric acid (3-undecylmercapto-2-undecyloxy)propyl ester
18. (6-Mercaptopurine-9-β-D-ribofuranoside)-5'-phosphoric acid (3-undecylmercapto-2-undecyloxy) propyl ester
19. (5-Trifluoromethyluridine)-5'-phosphoric acid (3-decylmercapto-2-dodecyloxy)propyl ester
20. (5-Fluorouridine)-5'-phosphoric acid (3-undecylmercapto-2-dodecyloxy)propyl ester
21. (5-Trifluoromethyluridine)-5'-phosphoric acid (3-undecylmercapto-2-dodecyloxy)propyl ester
22. (6-Mercaptopurine-9-β-D-ribofuranoside)-5'-phosphoric acid (3-tetradecylmercapto-2-decyloxy) propyl ester
23. (5-Fluorouridine)-5'-phosphoric acid (3-tridecylmercapto-2-decyloxy)propyl ester
24. (2-Fluoroadenosine)-5'-phosphoric acid (3-dodecylmercapto-2-decyloxy)propyl ester
25. (2-Desoxy-2-fluoroadenosine)-5'-phosphoric acid (3-dodecylmercapto-2-decyloxy)propyl ester
26. (6-Mercaptopurine)-9-β-D-ribofuranoside)-5'-phosphoric acid dodecyl ester
27. (5-Fluorouridine)-5'-phosphoric acid hexadecyl ester
28. (5-Trifluoromethyiuridine)-5'-phosphoric acid eicosyl ester
29. (5-Fluorouridine)-5'-phosphoric acid dodecyl ester
30. (6-Mercaptopurine-9-β-D-ribofuranoside)-5'-phosphoric acid dodecyl ester

EXAMPLE 1

(5-Fluorouridine)-5'-phosphoric acid (3-dodecylmercapto-2-decyloxy)propyl ester 3.6 g (6.1 mmoles) of phosphoric acid (3-dodecylmercapto-2-decyloxy)propyl ester was treated twice with 30 ml of anhydrous pyridine and concentrated by evaporation. The residue was dissolved in 30 ml of anhydrous pyridine, treated with 2.76 g (9.1 mmoles) of 2,4,6-triisopropylbenzenesulfonic acid chloride under nitrogen and stirred at room temperature for 30 minutes. Then, 1.60 g (6.1 mmoles) of 5-fluorouridine (Fluka) was added, and the charge was allowed to stand under $N_2$ for 24 hours.

Hydrolysis was performed using 15 ml of water, the mixture was stirred for another 2 hours at room temperature, freed from solvent under vacuum, and stripped twice using a small amount of toluene. The residue was purified by column chromatography on LiChroprep® RP-18 with a linear gradient of methanol/water 7/1 to methanol as the eluant. The yield is 3.1 g (69% of theoretical amount); oil. $R_f$=0.24 ($CH_2Cl_2$/MeOH 8/2); $R_f$=0.55 ($CH_2Cl_2$/MeOH/$H_2O$ 6.5/2.5/0.4) on Merck 5715 TLC plates, silica gel 60 F.

The phosphoric acid (3-dodecylmercapto-2-decyloxy)-propyl ester was prepared as described in WO 92/03462.

EXAMPLE 2

(6-Mercaptopurine-9-β-D-ribofuranoside)-5'-phosphoric acid (3-dodecylmercapto-2-decyloxy) propyl ester 6.2 g (12.5 mmoles) of phosphoric acid (3-dodecylmercapto-2-decyloxy)propyl ester was treated with 5.7 g (18.75 mmoles) of 2,4,6-triisopropylbenzenesulfonic acid chloride as described in example 1 and subsequently with 3.55 g (11.25 mmoles) of 6-mercaptopurine-9-β-D-ribofuranoside and after 24 hours, this was hydrolyzed with water.

Then, 2.85 g of calcium acetate in 15 ml of water was slowly dropped therein, precipitating the crude calcium salt of the conjugate. After prolonged stirring the precipitate with acetone (1/10), 6 g of an amorphous crude product was obtained, having 72 area % according to HPLC.

The calcium salt was suspended in 350 ml of methanol, treated with 150 g of Amberlite IR 120 in the $Na^+$ form and stirred for 2 days.

Thereafter, the ion exchanger was removed, the filtrate was evaporated, and the residue was purified by column chromatography on LiChroprep® RP-18 with a linear gradient of methanol/water 5/1 to 9/1. The fractions containing product were evaporated in a vacuum, and the residue was stirred with acetone and dried. Yield: 3.52 g (41% of theoretical amount).

DC; $R_f$=0.45 (isopropanol/butyl acetate/conc. ammonia/water 50/30/5/15).

EXAMPLE 3

(6-Mercaptopurine-9-β-D-ribofuranoside)-5'-phosphoric acid (3-dodecylmercapto-2-decyloxy) propyl ester sodium salt Analogous to Example 2, 41.4 g of phosphoric acid (3-dodecylmercapto-2-decyloxy)propyl ester in 400 ml of anhydrous pyridine was reacted with 42.9 g of 2,4,6-triisopropylbenzenesulfonic acid chloride and subsequently with 23.7 g of 6-mercaptopurine-9-β-D-ribofuranoside. The crude calcium salt which was filtered by suction after hydrolysis and precipitation with 25 g of calcium acetate in 160 ml of water, was distributed between 500 ml of MTB and 250 ml of 2N HCl and stirred until completely dissolved in the organic phase. The organic phase was separated, washed with saturated sodium chloride solution and concentrated in a rotary evaporator. The residue was applied onto 80 g of LiChroprep RP-18 (treat MTB solution of crude product with RP-18, evaporate and dry), and separated portion by portion in a pre-column on RP-18. Each time, a mixture of 3.7 l of methanol, 400 ml of water, 3 ml of glacial acetic acid, and 2 g of sodium acetate served as the eluant. The fractions containing product were combined, the desired compound was precipitated by adding 20 g of calcium acetate in 100 ml of water and filtered by suction. Yield: 32 g (43% of theoretical amount).

The calcium salt was suspended in 250 ml of MTB, extracted with 80 ml of 2N HCl by shaking, and the organic phase was washed twice with saturated sodium chloride solution. Following removal of the solvent, the residue was dissolved in 200 ml of toluene and adjusted to pH 7 against a Friscolyt electrode with 30% sodium methylate solution. The sodium salt was precipitated by stirring into 200 ml of acetone, filtered by suction and dried in a vacuum drying oven. Yield: 29 g (37% of theoretical amount).

$R_f$ value: 0.18 (Silica gel; eluant: isopropanol/butyl acetate/water/conc. ammonia 50/30/15/5).

EXAMPLE 4

(6-Mercaptopurine-9-β-D-riboturanoside)-5'-phosphoric acid (3-dodecylmercapto-2-decyloxy) propyl ester sodium salt Analogous to Example 3, the crude conjugate was prepared from 40 g of 6-mercaptopurine-9-β-D-ribofuranoside. The crude product was purified by column chromatography using 8 g each time, on a column with DIOL phase (diameter 4 cm; length 25 cm) (detection at 254 nm; eluant: methanol/MTB 10/4). The applied sample had clearly dissolved in the eluant. The product-containing fractions of the different separations were combined, evaporated and precipitated as the sodium salt from toluene and acetone as in Example 3. Yield: 64.5 g (51% of theoretical amount).

$R_f$ value: 0.85 (DIOL phase; eluant: methanol).

EXAMPLE 5

(6-Methylmercaptopurine-9-β-D-riboturanosidel-5'-phosphoric acid (3-dodecylmercapto-2-decyloxy) propyl ester sodium salt Analogous to Example 1, 14.9 g of 6-methylmercaptopurine-9-β-D-ribofuranoside (50 mmoles) were reacted with the mixed anhydride prepared from 27.3 g of phosphoric acid (3-dodecylmercapto-2-decyloxy)propyl ester and 25 g of 2,4,6-triisopropylbenzenesulfonic acid chloride in 250 ml of anhydrous pyridine, hydrolyzed and concentrated by evaporation. Analogous to Example 3, the crude product (HPLC: 67 area %) was purified by chromatography on RP-18, precipitated as the calcium salt, and converted to the sodium salt. Yield: 15.2 g (38% of theoretical amount).

$R_f$ value: 0.22 (Silica gel; eluant: isopropanol/butyl acetate/water/conc. ammonia 50/30/15/5).

EXAMPLE 6

(5-Fluorouridine)-5'-phosphoric acid (3-dodecylmercapto-2-decyloxy)propyl ester sodium salt Analogous to Example 1, 50 g of 5-fluorouridine was converted to the crude conjugate, precipitated as the calcium salt as described in Example 3 and subsequent to conversion to the free acid, was purified as the crude product by chromatography, analogous to Example 4, on a DIOL phase using methanol/MTB 10/4 as the eluant. The sodium salt prepared as in Example 3 was isolated in a yield of 69%.

$R_f$ value: 0.35 (DIOL plates; eluant: methanol/MTB 10/4).

EXAMPLE 7

$IC_{50}$ values (μg/ml) for Azathioprine, 6-Mercaptopurine (6-MP), 6-Mercaptopurinriboside, 6-MPR-DMDOPE and Doxorubicin in CFU-E and CFU-GM assays This table shows the $IC_{50}$ values μg/ml) for Azathioprine, 6-Mercaptopurine (6-MP) and 6-Mercaptopurinriboside in comparison to the (6-Mercaptopurine-9-β-D-ribofuranoside)-5'-phosphoric acid (3-dodecylmercapto-2-decyloxy) propyl ester 6-MPR-DMDOPE for in vitro cytotoxicity on murine bone marrow stern cells, including colony-forming units/erythrocytes (CFU-E) and colony-forming units/granulocytes-macrophages (CFU-GM). The cytostatic/cytotoxic compound Doxorubicin was also included as reference substance. All compounds were tested in 3–6 different experiments concentration dependently with, at least, doublicate or triplicate inclubations per concentration tested.

As can be seen from the results, 6-MPR-DMDOPE is much better tolerated by the bone marrow stern cells compared to all other compounds tested, in particular, in comparison to 6-Mercaptopurinriboside.

$IC_{50}$ values (μg/ml) for Azathioprine, 6-Mercaptopurine (6-MP), 6-Mercaptopurinriboside, 6-MPR-DMDOPE and Doxorubicin in CFU-E and CFU-GM assays.[a]

| Compound | CFU-E | | CFU-GM | |
|---|---|---|---|---|
| Azathioprine | 0.0004 + 0.0001 | (4) | 0.0043 + 0.0019 | (3) |
| 6-MP | 0.0003 + 0.0001 | (4) | 0.0023 + 0.00009 | (3) |
| 6-MP-/Riboside | 0.0003 + 0.0001 | (4) | 0.0023 + 0.00013 | (3) |
| 6-MPR-DMDOPE | 0.056 + 0.013 | (5) | 0.247 + 0.044 | (6) |
| Doxorubicin | 0.0017 + 0.0005 | (4) | 0.050 + 0.004 | (4) |

[a]Mean ± SEM; n, number of different experiments.

EXAMPLE 8

Bone marrow toxicity of 6-MPR-DMDOPE, Azathioprine, 6-Mercaptopurine and 6-Mercaptopurinriboside in female Balb/c mice: Day +4 (Exp. 930740)

Exp. 930740 shows the bone marrow toxicity of 6-MPR-DMDOPE, Azathioprine, 6-Mercaptopurine and 6-Mercaptopurinriboside in vivo in female Balb/c mice which were treated once daily p.o. for four consecutive days (day 0–day +3). The animals were killed on day +4 and bone marrow cellularity (cells/fernur) was determined. The results indicate no bone marrow toxicity for the 6-Mercaptopurinriboside ether lipid conjugate 6-MPR-DMDOPE up to the highest dose tested, i.e. 100 mg·kg$^{-1}$ day$^{-1}$ which corresponds on a molar basis with 30 mg·kg$^{-1}$ day$^{-1}$ 6-Mercaptopurinriboside. This latter compond shows, in contrast to the ether lipid conjugate 6-MPR-DMDOPE, clearly a dose-dependent reduciton in one marrow cellularity. The same finding was obtained for the other substances, including Azathioprine and 6-Mercaptopurine.

Bone marrow toxicity of 6-MPR-DMDOPE, Azathioprine, 6-Mercaptopurine and 6-Mercaptopurinriboside in female Balb/c mice: Day ± 4 (Exp. 930740)

| Compound | Dose (mg · kg$^{-1}$day$^{-1}$) | Cells/femur (10$^6$) |
|---|---|---|
| Control (0,5% Tylose) | — | 15.9 + 1.4 (8) $^a$ |
| Azathioprine | 10 | 11.6 + 0.4 (9) * |
| Azathioprine | 30 | 9.6 + 0.9 (9) ** |
| 6-Mercaptopurine | 10 | 13.0 + 1.5 (8) |
| 6-Mercaptopurine | 30 | 6.5 + 0.7 (9) ** |
| 6-Mercaptopurinriboside | 10 | 12.6 + 0.5 (9) ** |
| 6-Mercaptopurinriboside | 30 | 9.3 + 0.5 (9) ** |
| 6-MPR-DMDOPE | 30 | 15.4 + 0.9 (9) |
| 6-MPR-DMDOPE | 100 | 13.0 + 0.6 (9) |

$^a$mean ± SEM, Treatment once daily p.o., day 0-day + 3 Sacrifice on day +4
\* P ≦ 0.05 Mann-whitney-test
\*\* P ≦ 0.01

EXAMPLE 9

Bone marrow toxicity of 6-MPR-DMDOPE, Azathioprine, 6-Mercaptopurine, 6-Mercaptopurinriboside and Cyclosporin A in female Balb/c mice: Day +4 (Exp. 940026).

Exp. 940026 is an experiment which was aimed at reproducing the results obtained in Exp. 930740 (Example 8). In this experiment Cyclosporin A was included as a reference compound, too. The outcome of the Exp. 940026 confirmed the results obtained in Exp. 930740 in vivo.

Bone marrow toxicity of 6-MPR-DMDOPE, Azathloprine, 6-Mercaptopurine, and Cyclosporin A in female Balb/c mice: Day + 4 (Exp. 940026)

| Compound | Dose (mg · kg$^{-1}$ day$^{-1}$) | Cells/femur (10$^6$) |
|---|---|---|
| control (0.5% Tylose) | — | 15.6 ± 0.8 (10) a |
| Azathioprine | 10 | 11.1 ± 0.6 (10) ** |
| Azathloprine | 30 | 9.1 ± 0.5 (10) ** |
| 6-Mercaptopurine | 10 | 10.9 ± 0.9 (10) * |
| 6-Mercaptopurine | 30 | 6.2 ± 0.5 (10) ** |
| 6-Mercaptopurinriboside | 10 | 13.7 ± 1.4 (10) * |
| 6-Mercaptopurinriboside | 30 | 8.4 ± 0.4 (10) ** |
| 6-MPR-DMDOPE | 30 | 14.3 ± 0.5 (10) |
| 6-MPR-DMDOPE | 100 | 13.0 ± 0.4 (10) |
| Cyclosporin A | 5 | 13.1 ± 0.4 (10) |
| Cyclosporin A | 10 | 7.6 ± 1.4 (10) ** |

$^a$mean + SEM; Treatment once daily p.o., day 0 – day + 3 Sacrifice on day + 4
\*p ≦ 0.05
\*\*p ≦ 0.01  } Mann-Whitney-test

EXAMPLE 10

Bone marrow toxicity ($\mu$M) of 5-FU-DMDOPE and 5-FU in CFU-E and CFU-GM assays.

The table shown in Encl. 4 gives the mean IC$_{50}$ values for 5-Fluorouridine (5-FU) and the (5-Fluorouridine) -5'-phosphoric acid (3-dodecylmercapto 2 decyloxy) propyl ester (5-FU-DMDOPE) for bone marrow toxicity in vitro in CFU-E and CFU-GM assays. For assay conditions, please refer to description of Example 7.

The data indicate that the ether lipid conjugate of 5-Fluorouridine (5-FU-DMDOPE) is 610 times and 238 times less toxic on erythirocyte and granulocyte/macrophage bone marrow stem cells, respectively, compared to 5-FU itself.

Bone marrow toxicity ($\mu$M) of 5-FU-DMDOPE and 5-FU in CFU-E and CFU-GM assays

| Compound | CFU-E$^a$ | CFU-GM$^a$ |
|---|---|---|
| 5-FU-DMDOPE | 0.372 (3) | 1.178 (7) |
|  | 610 × | 238 × |
| 5-FU | 0.00061 (3) | 0.00496 (10) |

$^a$Mean; n, number of experiments

EXAMPLE 11

Influence of the 5-FU ether lipid conjugate 5-FU-DMDOPE (FIG. 1) and of 5-FU (FIG. 2) on the L 1210 leukemia in vivo: Survival time.

Figure 1:
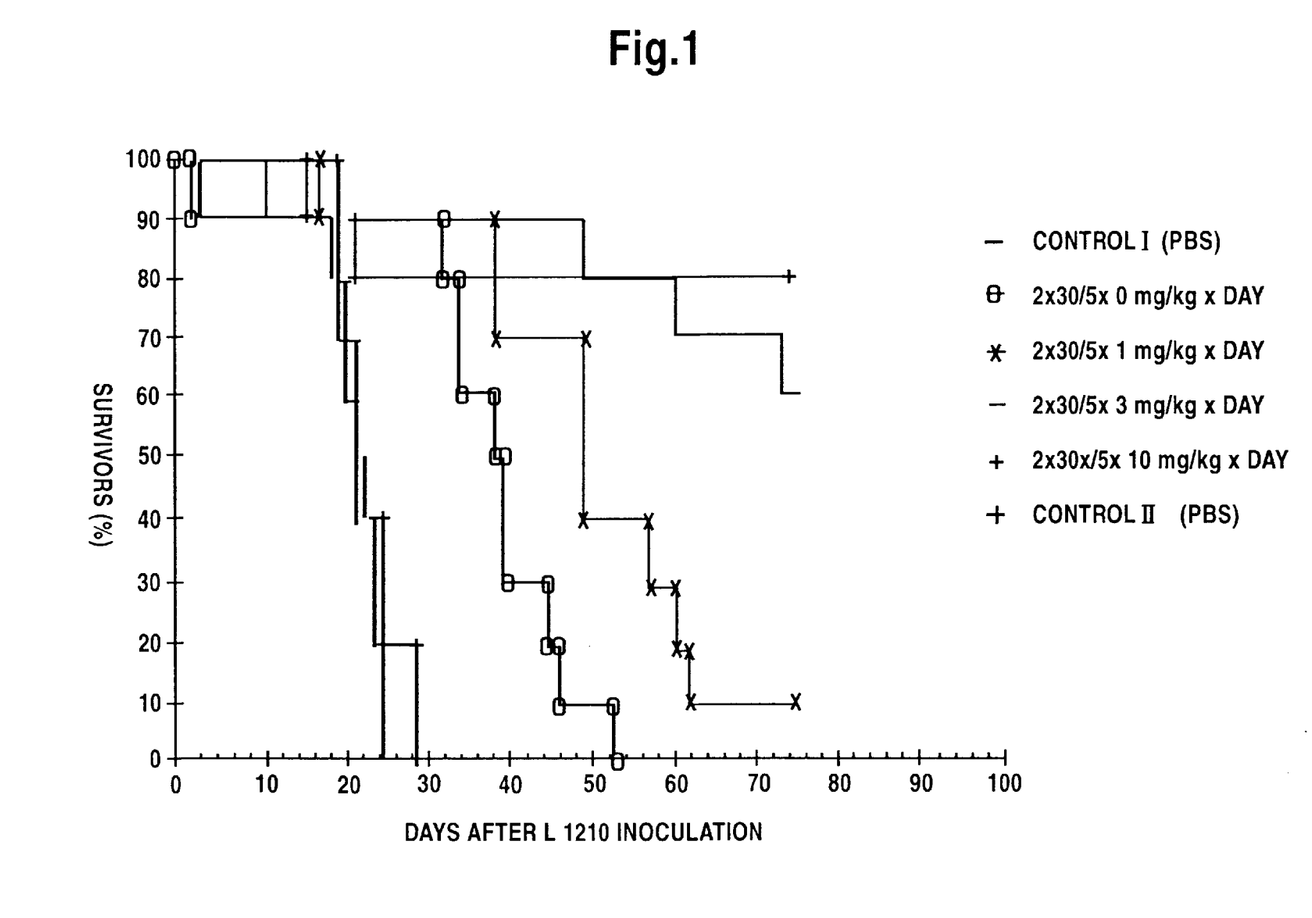
FIG. 1 shows the influence of 5-FU-DMDOPE on the L1210 leukemia in vivo.
Figure 2:
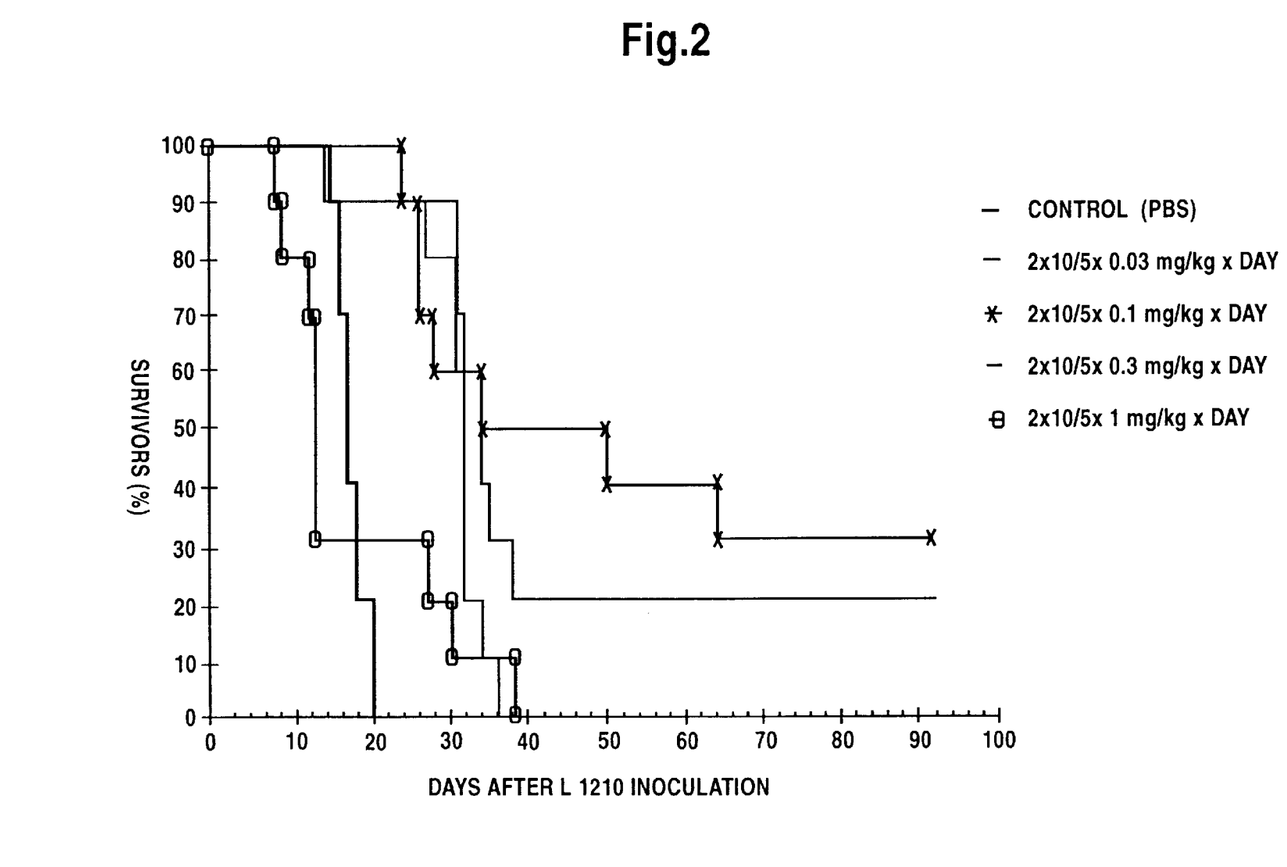
FIG. 2 shows the influence of 5-FU on the 1201 Leukemia in vivo.

Mice were inoculated with L 1210 leukemia cells on day 0 (n=10 animals/group) and w ere then treated once daily i.p. from day 0 (+1 h)–day +41 (6 weeks) with the weekly cycles indicated on FIGS. 1 and 2, respectively.

From the survival curves of the control and treatment groups shown on FIG. 2 it is obvious, that 5-FU has, as reported in the literature, a very narrow dose-efficacy profile, i.e. icreasing the dose, for example from 2×10/5×0.1 mg·kg$^{-1}$ day$^{-1}$ to 2×10/5×0.3 mg·kg$^{-1}$ day$^{-1}$ or to even higher doses lead to reduced survival rates.

In contrast, with the 5-FU ether lipid conjugate 5-FU-DMDOPE a clear dose-dependent increase in survival time was obtained compared to control I and II (FIG. 1) indicating that equimolar doses of 5-FU-DMDOPE are clearly more effective in this leukemia model compared to the standard compound 5-FU.

Taken into consideration that 5-FU-DMDOPE is more effective (FIGS. 1 and 2) and much less toxic on bone marrow cells it can be concluded that 5-FU-DMDOPE has a much higher therapeutic index/ratio compared to the standard cytostatic 5-FU.

We claim:

1. A nucleoside monophosphate derivative of formula (I)

(I)

wherein $R^1$ is selected from the group consisting of a straight-chain or branched, saturated or unsaturated alkyl chain having 1–20 carbon atoms, which is unsubstituted or substituted at least once by halogen, $C_1$–$C_6$ alkoxy, $C_1$–$C_6$ alkylmercapto, $C_1$–$C_6$ alkoxycarbonyl, $C_1$–$C_6$ alkysulfinyl, or $C_1$–$C_6$ alkylsulfonyl groups;

$R^2$ is selected from the group consisting of hydrogen, a straight-chain or branched, saturated or unsaturated alkyl chain having 1–20 carbon atoms, which is unsubstituted or substituted at least once by halogen, $C_1$–$C_6$ alkoxy, $C_1$–$C_6$ alkylmercapto, $C_1$–$C_6$ alkoxycarbonyl, or $C_1$–$C_6$ alkylsulfonyl group;

$R^3$ is selected from the group consisting of hydrogen, hydroxy, azido, amino, cyano, and halogen;

$R^4$ is selected from the group consisting of hydroxy, azido, amino, cyano, and halogen;

$R^5$ is selected from the group consisting of hydrogen, hydroxy, azido, amino, cyano, and halogen;

X is selected from the group consisting of a valence bond, sulfur, a sulfinyl group and a sulfonyl group;

Y is selected from the group consisting of a valence bond, and an oxygen atom;

B is a purine or pyrimidine base selected from formulas III (a–d)

(IIIa)

(IIIb)

(IIIc)

(IIId)

wherein
$R^6$ is selected from the group consisting of hydrogen; an alkyl chain having 1–6 carbon atoms, which is unsubstituted or substituted by halogen; an alkenyl or alkinyl residue having 2–6 carbon atoms, which is unsubstituted or substituted by halogen, and halogen;

$R^{6'}$ is selected from the group consisting of a hydrogen atom, a benzyl residue and a phenylthio residue;

$R^7$ is selected from the group consisting of hydrogen; an alkyl chain having 1–6 carbon atoms, which is unsubstituted or substituted by halogen; and halogen;

$R^8$ is selected from the group consisting of hydrogen, an alkyl chain having 1–6 carbon atoms, halogen, a hydroxy group and an amino group;

$R^9$ is selected from the group consisting of hydrogen, an amino group and a halogen atom; and $R^{10}$ is selected from the group consisting of hydrogen; halogen; mercapto; hydroxy; $C_1$–$C_6$ alkoxy; $C_1$–$C_6$ alkylmercapto; and an amino group which is unsubstituted or substituted at least once by $C_1$–$C_6$ alkyl; $C_1$–$C_6$ alkoxy; hydroxy-$C_2$–$C_6$ alkyl; $C_3$–$C_6$ cycloalkyl; aryl, hetaryl, aralkyl, or hetarylalkyl groups or a $C_2$–$C_6$ alkenyl which is unsubstituted or substituted by mono- or dialkyl or alkoxy groups; wherein said aryl, hetaryl, aralkyl, or hetarylalkyl groups are unsubstituted or substituted at the aryl or hetaryl residue by at least one mercapto, hydroxy, $C_1$–$C_6$ alkoxy group, $C_1$–$C_6$alkyl group or halogen;

with the proviso that at least one of the residues $R^3$ or $R^5$ is hydrogen; their tautomers, their optically active forms and racemic mixtures, and their physiologically acceptable salts of inorganic and organic acids or bases.

2. The nucleoside monophosphate derivative according to claim 1, wherein $R^1$ is a straight-chain $C_8$–$C_{15}$ alkyl group which is unsubstituted or substituted by a $C_1$–$C_6$ alkoxy or a $C_1$–$C_6$ alkylmercapto group.

3. The nucleoside monophosphate derivative according to claim 1, wherein $R^2$ represents a straight-chain $C_8$–$C_{15}$ alkyl group which is unsubstituted or substituted by a $C_1$–$C_6$ alkoxy or a $C_1$–$C_6$ alkylmercapto group.

4. The nucleoside monophosphate derivative according to claim 1, wherein X is sulfur, sulfinyl or sulfonyl, and Y is oxygen.

5. The nucleoside monophosphate derivative according to claim 1, wherein X and Y are valence bonds, $R^2$ is hydrogen, and $R^1$ is a $C_1$–$C_{20}$ alkyl chain which is unsubstituted or substituted by $C_1$–$C_6$ alkoxy or a $C_1$–$C_6$ alkylmercapto.

6. The nucleoside monophosphate derivative according to claim 1, wherein $R^5$ is selected from the group consisting of hydrogen, azido, cyano, and halogen.

7. The nucleoside monophosphate derivative according to claim 1, wherein $R^3$ and $R^4$ are individually selected from the group consisting of a hydroxy, cyano or azido group or a halogen atom.

8. The nucleoside monophosphate derivative according to claim 1, wherein $R^6$ and $R^7$ are individually selected from the group consisting of a hydrogen atom; a $C_1$–$C_6$ alkyl residue which is unsubstituted or substituted by halogen; a halogen atom; and a $C_2$–$C_6$ alkenyl or alkinyl group which is unsubstituted or substituted by halogen.

9. The nucleoside monophosphate derivative according to claim 1, wherein $R^8$ is selected from the group consisting of a hydrogen atom, a $C_1$–$C_6$ alkyl residue, an amino group, and a halogen atom.

10. The nucleoside monophosphate derivative according to claim 1, wherein $R^{10}$ is selected from the group consisting of a hydrogen or halogen atom, a $C_1$–$C_6$ alkoxy mercapto, a $C_1$–$C_6$ alkylmercapto, and an amino group wherein said amino group is unsubstituted or substituted at least once by a $C_1$–$C_6$ alkyl, a hydroxy-$C_2$–$C_6$ alkyl, a $C_3$–$C_6$ cycloalkyl, or an aryl or aralkyl residue, wherein said aryl or aralkyl residue is unsubstituted or substituted by at least one hydroxy, $C_1$–$C_6$alkoxy or $C_1$–$C_6$ alkyl group, or by a halogen atom.

11. The nucleoside monophosphate derivative according to claim 1, wherein $R^1$ is a straight-chain $C_9$–$C_{13}$ alkyl group which is unsubstituted or substituted by a methoxy, ethoxy, butoxy, hexyloxy, methylmercapto, ethylmercapto, propylmercapto, butylmercapto, or hexylmercapto residue;

$R^2$ is a straight-chain $C_8$–$C_{14}$ alkyl group which is unsubstituted or substituted by a methoxy, ethoxy, propoxy, butoxy, hexyloxy, methylmercapto, ethylmercapto, propylmercapto, butylmercapto, or hexylmercapto residue;

$R^3$ is a hydroxy, cyano, azido or fluorine residue;

$R^4$ is a hydroxy, cyano, azido, or fluorine residue;

$R^5$ is hydrogen;

$R^6$ is selected from the group consisting of hydrogen; a methyl, trifluoromethyl, ethyl, vinyl, propenyl, ethinyl, or propinyl residue; and a fluorine, chlorine or bromine atom;

$R^{6'}$ is hydrogen;

$R^7$ is selected from the group consisting of hydrogen; a methyl, ethyl, vinyl, propenyl, ethinyl, or propinyl residue; and a chlorine or bromine atom; and $R^{10}$ is selected from the group consisting of hydrogen; a methoxy, ethoxy, propoxy, butoxy, hexyloxy, mercapto, methylmercapto, ethylmercapto, butylmercapto, or hexylmercapto residue; and an amino group which is unsubstituted or substituted by thienyl, furyl, pyridyl, thienylmethyl, furylmethyl, or pyridylmethyl.

12. The nucleoside monophosphate derivative according to claim 1, wherein the nucleoside portion is selected from the group consisting of:

6-mercaptopurine-9-β-d-ribofuranoside, 5-fluorouridine, inosine, 5-methyluridine, 2',3'-didesoxy-2',3'-difluorothymidine, 5-chlorouridine, 5-trifluoromethyluridine, 5-ethinyluridine, 5-ethinylcytidine, 5-prop-1-enyluridine, 5-prop-2-enyluridine, adenosine, guanosine 2,6-diaminopurine-9-β-D-ribofuranoside, 2-amino-6-mercapto-purine-9-β-D-ribofuranoside, 2-amino-6-methylmercapto-purine-9-β-D-ribofuranoside, 2-amino-6-chloropurine-9-β-D-ribofuranoside, 2'-desoxy-2'-aminoadenosine, 2'-desoxy-2'-azidoadenosine, 2'-desoxy-2'-azidocytidine, 2'-desoxy-5-fluorouridine, 2-chloroadenosine, 2-fluoroadenosine, 3'-desoxy-5-fluoroadenosine, 6-methylmercaptopurine-9-β-D-ribofuranoside, 2-bromoadenosine, and 2-fluoro-2'-desoxyadenosine.

13. The nucleoside triphosphate derivative according to claim 1, wherein $R^{10}$ is selected from the group consisting of hydrogen; a methoxy, ethoxy, propoxy, butoxy, hexyloxy, mercapto, methylmercapto, ethylmercapto, butylmercapto, or hexylmercapto residue; an amino group which is unsubstituted or substituted by thienyl, furyl, pyridyl, thienylmethyl, furylmethyl, or pyridylmethyl.

14. The nucleoside triphosphate derivative according to claim 1, wherein said nucleoside triphosphate derivative is selected from the group consisting of (5-Fluorouridine)-5'-phosphoric acid (3-dodecylmercapto-2-decyloxy)propyl ester, (6-Mercaptopurine-9-β-D-ribofuranoside)-5'-phosphoric acid (3-dodecylmercapto-2-decyloxy)propyl ester, (6-Methylmercaptopurine-9-β-D-ribofuranoside)-5'-phosphoric acid (3-dodecylmercapto-2-decyloxy)propyl ester sodium salt, their tautomers, their optically active forms and racemic mixtures, and their physiologically acceptable salts of inorganic and organic acids or bases.

15. A composition comprising at least one compound according to claim 1 in combination with a pharmaceutically acceptable adjuvant or vehicle.

16. A composition comprising at least one compound according to claim 14 in combination with a pharmaceutically acceptable adjuvant or vehicle.

17. A method for treating malignant tumors comprising administering to a patient in need of such treatment an amount of the composition according to claim 15 effective to treat said tumor.

18. A method for treating malignant tumors comprising administering to a patient in need of such treatment an amount of the composition according to claim 16 effective to treat said tumor.

19. The method according to claim 17, wherein said tumor is selected from the group consisting of neoplasms, carcinomas, sarcomas and leukemias.

20. A method for suppressing immune activity in a patient in need of such treatment, comprising administering to a patient in need of such treatment, an immunosuppressive amount of the composition according to claim 15.

21. A method for suppressing immune activity in a patient in need of such treatment, comprising administering to a patient in need of such treatment, an immunosuppressive amount of the composition according to claim 16.

22. The method according to claim 20, wherein said patient has an organ specific or generalized auto immune disease.

23. The method according to claim 21, wherein said patient has an organ specific or generalized auto immune disease.

24. The method according to claim 20, wherein said method suppresses allogenic or semi-allogenic graft rejection.

25. The method according to claim 21, wherein said method suppresses allogenic or semi-allogenic graft rejection.

* * * * *